US012758216B2

(12) United States Patent
Choi

(10) Patent No.: US 12,758,216 B2
(45) Date of Patent: Oct. 13, 2026

(54) END TOOL AND SURGICAL INSTRUMENT

(71) Applicant: LIVSMED INC., Seongnam-si (KR)

(72) Inventor: Woo Jung Choi, Siheung-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 19/054,319

(22) Filed: Feb. 14, 2025

(65) Prior Publication Data

US 2025/0302471 A1 Oct. 2, 2025

(30) Foreign Application Priority Data

Mar. 27, 2024 (KR) ........................ 10-2024-0041884

(51) Int. Cl.
*A61B 17/068* (2006.01)
*A61B 17/00* (2006.01)

(52) U.S. Cl.
CPC .. *A61B 17/068* (2013.01); *A61B 2017/00477* (2013.01)

(58) Field of Classification Search
CPC .................... A61B 17/068; A61B 2047/00477
See application file for complete search history.

(56) References Cited

U.S. PATENT DOCUMENTS 9,060,770 B2 * 6/2015 Shelton, IV ....... A61B 17/0682
2011/0290853 A1 12/2011 Shelton, IV

FOREIGN PATENT DOCUMENTS

WO 2018/118234 A1 6/2018
WO WO-2024054080 A1 * 3/2024 ....... A61B 17/07207

* cited by examiner

*Primary Examiner* — Michelle Lopez
(74) *Attorney, Agent, or Firm* — Bridgeway IP Law Group, PLLC; Sang Ho Lee; Hyun Woo Shin

(57) ABSTRACT

Provided are an end tool and a surgical instrument. The end tool of a surgical instrument, which is coupled to one end of a connection part of an external device, includes a first jaw rotatable about a pitch rotation shaft and a second jaw relatively rotatable with respect to the first jaw about a second jaw rotation shaft disposed in the first jaw parallel to the pitch rotation shaft, wherein the first jaw and the second jaw are opposed to each other and perform an opening or closing operation, and the first jaw rotates about the pitch rotation shaft but rotates in a direction opposite to a rotation direction of the second jaw in response to the second jaw rotating about the second jaw rotation shaft.

19 Claims, 14 Drawing Sheets

END TOOL AND SURGICAL INSTRUMENT

CROSS-REFERENCE TO RELATED APPLICATION

This application is based on and claims priority under 35 USC § 119 to Korean Patent Application No. 10-2024-0041884, filed on Mar. 27, 2024, in the Korean Intellectual Property Office, the disclosure of which is incorporated by reference herein in its entirety.

BACKGROUND

1. Field

The present disclosure relates to end tools and surgical instruments.

2. Description of the Related Art

In medical terms, surgery refers to curing an illness by cutting, slitting, or manipulating the skin, mucous membranes, or other tissues using medical devices. In particular, open surgery, which involves cutting to open the skin at a surgical site and treating, shaping, or removing organs therein, causes problems, such as bleeding, side effects, patients' pain, and scarring. Therefore, recently, surgery performed by forming a predefined hole in the skin and inserting a medical device, such as a laparoscope, surgical instrument, or microsurgical microscope, or surgery using a robot, has come into prominence as an alternative.

A surgical instrument is a tool for operating on a surgical site by manipulating an end tool provided at one end of a shaft passing through a hole perforated in the skin directly by a doctor with his hands or using a robot arm. The end tool provided in the surgical instrument performs rotation, gripping, cutting, etc. through a certain structure.

The related art described above is technical information that the inventor possessed for deriving the present disclosure or acquired in the process of deriving the present disclosure and should not be considered as known art disclosed to the general public before filing the application for the present disclosure.

SUMMARY

The present disclosure relates to an end tool and a surgical instrument using the end tool for use in laparoscopic surgery or various other surgeries, capable of improving user convenience by simulating an anvil-centric motion without having an anvil-centric design.

Additional aspects will be set forth in part in the description which follows and, in part, will be apparent from the description, or may be learned by practice of the presented embodiments of the disclosure.

One aspect of the present disclosure provides an end tool of a surgical instrument, which is coupled to one end of a connection part of an external device, including a first jaw rotatable about a pitch rotation shaft and a second jaw relatively rotatable with respect to the first jaw about a second jaw rotation shaft disposed in the first jaw parallel to the pitch rotation shaft, wherein the first jaw and the second jaw are opposed to each other and perform an opening or closing operation, and the first jaw rotates about the pitch rotation shaft but rotates in a direction opposite to a rotation direction of the second jaw in response to the second jaw rotating about the second jaw rotation shaft.

In the present disclosure, during the opening or closing operation of the first jaw and the second jaw, an angle formed by the second jaw and the connection part may be maintained constant, and an angle formed by the first jaw and the second jaw may change as the first jaw pitch-rotates.

In the present disclosure, when the first jaw rotates in response to the rotation of the second jaw, the first jaw may pitch-rotate at a same rotation angle as a rotation angle of the second jaw or pitch-rotate at a rotation angle of a preset ratio with respect to the rotation angle of the second jaw.

In the present disclosure, the second jaw rotation shaft may share the same axis as the pitch rotation shaft.

In the present disclosure, when the first jaw rotates in response to the rotation of the second jaw, the first jaw may pitch-rotate at a same rotation angle as the rotation angle of the second jaw.

In the present disclosure, a rotation angle range of second jaw may be +90° to −90° based on an extension direction (an X-axis) of the connection part, a rotation angle range of first jaw may be $+90-\theta_1°$ to $-90-\theta_1°$ based on the extension direction (the X-axis) of the connection part, and $\theta_1$ may be an angle between the first jaw and the second jaw during the opening operation.

In the present disclosure, the end tool may include a first function that implements the opening or closing operation of the first jaw and the second jaw by the first jaw rotating about the pitch rotation shaft in response to the second jaw rotating about the second jaw rotation shaft and a second function that implements the opening or closing operation of the first jaw and the second jaw by the second jaw rotating while the first jaw is fixed, wherein the end tool is selected and driven by one of the first function and the second function.

In the present disclosure, the end tool may further include an end tool hub connecting the connection part to the first jaw and the second jaw, wherein the end tool hub may include a first end tool hub formed to accommodate at least a portion of the first jaw therein and a second end tool hub axially coupled to the first end tool hub and rotatable relative to the first end tool hub.

In the present disclosure, the first end tool hub and the second end tool hub may be axially coupled through the pitch rotation shaft, and the end tool hub may include a pitch pulley rotatable about the pitch rotation shaft and a pitch wire at least partially wound around the pitch pulley to transmit driving force to the pitch pulley.

In the present disclosure, the pitch pulley may include a coupling part fixedly coupling the pitch pulley to the first end tool hub, and the first end tool hub may rotate integrally with the pitch pulley by the coupling part.

In the present disclosure, the end tool may further include a fastening member coupled to the pitch wire to couple the pitch pulley to the pitch wire.

In the present disclosure, the pitch wire may be formed as a single wire, and the fastening member may be fastened to a portion of the pitch wire.

In the present disclosure, the pitch pulley may include a fastening recess to which the fastening member is coupled.

In the present disclosure, when the end tool is in a neutral state, an imaginary line connecting a center of the pitch pulley to the fastening recess may form an angle of 0° to +900 with an extension direction (the X-axis) of the connection part.

In the present disclosure, the first end tool hub and the first jaw may be axially coupled through the pitch rotation shaft, and the end tool hub may include a pitch pulley rotatable about the pitch rotation shaft and a pitch wire at least partially wound around the pitch pulley to transmit driving force to the pitch pulley.

In the present disclosure, the end tool hub may include an auxiliary pulley rotation shaft parallel to the pitch rotation shaft and located adjacent to the pitch rotation shaft and a pitch auxiliary pulley rotating about the auxiliary pulley rotation shaft.

In the present disclosure, both strands of the pitch wire wound around the pitch pulley and extending to the connection part may be disposed on a same side with respect to the auxiliary pulley rotation shaft.

In the present disclosure, a diameter of the pitch auxiliary pulley may be smaller than a diameter of the pitch pulley.

In the present disclosure, the pitch wire may be located on a common internal tangent line of the pitch pulley and the pitch auxiliary pulley, a rotation angle of the pitch pulley may be expanded by the pitch auxiliary pulley, and a rotation angle range of the second jaw may be expanded by an additional angle set by the pitch auxiliary pulley.

Another aspect of the present disclosure provides an end tool of a surgical instrument, which is coupled to one end of a connection part of an external device, including a first jaw and a second jaw each configured to be rotatable, a pitch rotation shaft that is a center of pitch rotation of the first jaw or the second jaw, a pitch pulley formed to be rotatable about the pitch rotation shaft, a pitch wire at least partially wound around the pitch pulley to transmit driving force to the pitch pulley, a fastening member coupled to the pitch wire to couple the pitch pulley to the pitch wire, an auxiliary pulley rotation shaft disposed parallel to the pitch rotation shaft and adjacent to the pitch rotation shaft, and a pitch auxiliary pulley rotating about the auxiliary pulley rotation shaft, wherein the pitch pulley includes a fastening recess into which the fastening member is coupled, and when the end tool is in a neutral state parallel to an extension direction of the connection part, an imaginary line connecting a center of the pitch pulley to the fastening recess forms an angle of 0° to +90° with the extension direction (an X-axis) of the connection part.

Another aspect of the present disclosure provides a surgical instrument including an end tool rotatable in two or more directions, a manipulation part controlling rotation of the end tool, and a connection part extending in a first direction (an X-axis) and having one end portion to which the end tool is coupled and another end portion to which the manipulation part is coupled, wherein the end tool includes a first jaw rotatable about a pitch rotation shaft and a second jaw relatively rotatable with respect to the first jaw about a second jaw rotation shaft disposed in the first jaw and parallel to the pitch rotation shaft, wherein the first jaw and the second jaw are opposed to each other and perform an opening or closing operation, and the first jaw rotates about the pitch rotation shaft but rotates in a direction opposite to a rotation direction of the second jaw in response to the second jaw rotating about the second jaw rotation shaft.

Other aspects, features and advantages in addition to those described above will become apparent from the following drawings, claims and detailed description of the invention.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
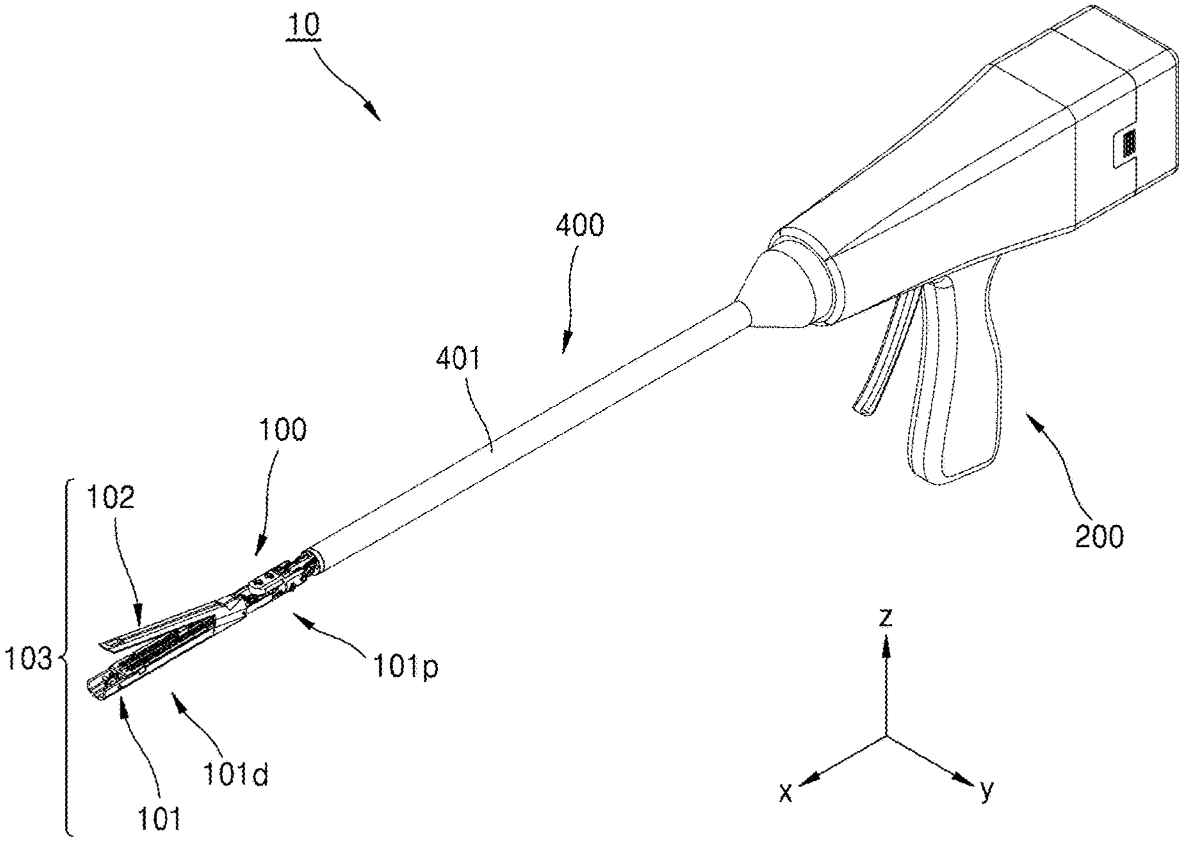
FIG. 1 is a perspective view showing a surgical instrument to which an end tool is applied according to a first embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions, such as "at least one of," when preceding a list of elements, modify the entire list of elements and do not modify the individual elements of the list.

Hereinafter, embodiments of the present invention are described with reference to the accompanying drawings, in which like numbers refer to like elements throughout and a redundant description thereof is omitted.

As the present disclosure allows for various changes and numerous embodiments, certain embodiments are illustrated in the drawings and described in detail in the written description. The advantages and features of the embodiments and methods of achieving them are apparent from the following embodiments that are described in detail with reference to the accompanying drawings. However, the embodiments may have different forms and should not be construed as being limited to the descriptions set forth herein.

In the description of the present disclosure, when it is determined that the detailed description of the related art would obscure the gist of the present disclosure, the description thereof is omitted.

In the following embodiments, an expression used in the singular encompasses the expression of the plural, unless it has a clearly different meaning in the context. Terms such as first, second, and the like may be used to describe various components, but the components should not be limited by the terms. The above terms are used only for the purpose of distinguishing one component from another.

In the following embodiments, terms such as "including" or "having" means that the features or components described in the specification are present, and do not preclude the possibility that one or more other features or components are added.

In the following embodiments, when a part of a unit, area, component, etc. is said to be on or on another part, it is not only a case in which the part is directly on top of the other part, but also a case in which other units, areas, components, etc. are interposed therebetween.

In the following embodiments, terms, such as connecting or combining, do not necessarily mean a direct and/or fixed connection or combination of two members, unless the context clearly indicates otherwise, and do not exclude that another member is interposed between the two members.

In the drawings, the sizes of components may be exaggerated or reduced for convenience of description. For example, the size and thickness of each component shown in the drawings are arbitrarily shown for convenience of description, so the following embodiments are not necessarily limited to that shown.

FIG. 1 is a perspective view showing a surgical instrument to which an end tool is applied according to a first embodiment of the present disclosure.

Before describing an end tool 100 according to the first embodiment of the present disclosure, a surgical instrument 10 to which the end tool according to the first embodiment of the present disclosure is applicable is first described.

Referring to FIG. 1, the surgical instrument 10 to which the end tool according to the first embodiment of the present disclosure is applied may further include a manipulation part 200 and a connection part 400, in addition to the end tool 100.

Here, the connection part 400 is formed in the shape of a hollow shaft, and one or more wires and electric wires may be accommodated therein. The manipulation part 200 may be coupled to one end portion of the connection part 400, and the end tool 100 is coupled to the other end portion of the connection part 400, so that the connection part 400 serves to connect the manipulation part 200 to the end tool 100. As an example, the connection part 400 may include a straight part 401, and although not shown, the connection part 400 may also include one or more curved parts for ease of use and control of the configuration of manipulation.

The manipulation part 200 is formed at one end portion of the connection part 400 and provided as an interface to be directly controlled by a medical doctor, for example, a tongs shape, a stick shape, a lever shape, or the like, and when the medical doctor controls the manipulation part 200, the end tool 100, which is connected to the interface and inserted into the body of a surgical patient, performs a certain motion, thereby performing surgery. Here, in FIG. 1, although the manipulation part 200 is shown as being formed in the shape of a handle that closely adheres to the finger and may perform one or more operations, for example, pulling or pushing, the concept of the present disclosure is not limited thereto and various types of manipulation parts that may be connected to the end tool 100 and manipulate the end tool 100 may be possible.

The end tool 100 may be formed at the other end portion of the connection part 400 and may be inserted into a surgical site to perform necessary motions for surgery. As an example of the end tool 100, a pair of jaws 103 for performing a grip operation may be used. However, the concept of the present disclosure is not limited thereto, and various devices for surgery may be used as the end tool 100. For example, a configuration of a cantilever cautery may also be used as the end tool. The end tool 100 is connected to the manipulation part 200 by a power transmission part (not shown, for example, a wire, etc.) and receives driving force of the manipulation part 200 through the power transmission part to perform a motion necessary for surgery, such as gripping, cutting, suturing, or the like.

Here, the end tool 100 according to the first embodiment of the present disclosure is formed to be rotatable in at least one or more directions. For example, the end tool 100 may perform a pitch motion around a Y-axis of FIG. 1, perform a yaw motion around a Z-axis of FIG. 1, and perform an actuation motion around the Y-axis. Or, in another embodiment, the end tool may perform actuation motion around the Z-axis.

Meanwhile, the power transmission part (not shown) may connect the manipulation part 200 to the end tool 100 and serve to transmit driving force of the manipulation part 200 to the end tool 100 and may include a plurality of wires, pulleys, links, nodes, gears, etc.

In describing the present disclosure, a part close to a user, that is, a part close to the manipulation part 200 is referred to as a proximal end, and a part away from the user, that is, a part close to the end tool 100 is referred to as a distal end.

For example, a part of the end tool 100 close to the manipulation part 200 is defined as a proximal end **101*p* of the end tool 100, and a part away from the manipulation part 200, that is, close to an end portion of the end tool 100, is defined as a distal end 101*d* and described. From another perspective, the proximal end 101*p* of the end tool 100 may be described as a part close to the connection part 400, and the distal end 101*d* of the end tool 100 may be described as a part away from the connection part 400**.

Before describing characteristics of the end tool according to the first embodiment of the present disclosure, an anvil-centric design is described.

Referring to FIG. 1, the end tool 100 may include a first jaw 101 and a second jaw 102, and the first jaw 101 and the second jaw 102 may be open or closed. Here, an example of the end tool 100 may be a stapler. The end tool 100, which performs the function of a stapler, is described in detail below.

The first jaw 101 may be a jaw including a cartridge, and the second jaw 102 may be a jaw with an anvil formed on the side opposite to the first jaw 101. Here, for convenience, the second jaw 102 is referred to as an anvil and described.

There are two types of the end tool in performing a stapling operation after closing the first jaw 101 and the second jaw 102. In a first type, the first jaw stays in place and the second jaw 102, i.e., the anvil, rotates to be closed with the first jaw 101, and in a second type, the anvil stays in place and the first jaw 101 rotates to be closed with the anvil. Here, the second type of product is referred to as an anvil-centric design.

Products according to the related art are classified into a first type design and a second type design in terms of mechanical design of the end tool. The second type design is advantageous in terms of usability but has a high level of difficulty of design and limitations in terms of space utilization.

For example, in order to implement the anvil-centric design, a joint part for a yaw or pitch motion has to be fixed to the anvil and the first jaw 101 has to be able to rotate based on the anvil, and thus, all functional components for the stapling operation of the stapler has to be fixed to the anvil. For example, a fixing pulley of the first jaw 101, to be described below, should be placed on the anvil rather than the first jaw 101, but this may not be possible due to space constraints.

As such, the existing anvil-centric design has the disadvantage of being difficult to design, so the problem to be solved by the present disclosure is to enable the end tool 100 to implement an anvil-centric motion, while having the advantages of the first type design.

The present disclosure implements an anvil-centric motion by simulating an anvil-centric design without performing an anvil-centric design.

FIGS. 2A to 5B are conceptual diagrams illustrating a motion of the end tool according to selection of an anvil-centric function of the end tool according to the first embodiment of the present disclosure.

Figure 2B:
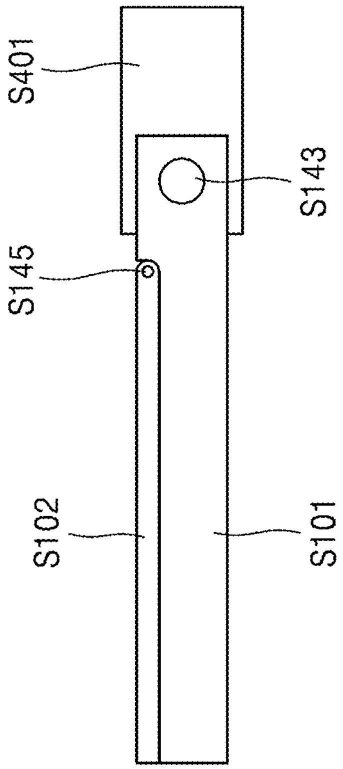
FIGS. 2A to 5B are conceptual diagrams illustrating motion of an end tool according to selection of an anvil-centric function of the end tool according to the first embodiment of the present disclosure.
Figure 2A:
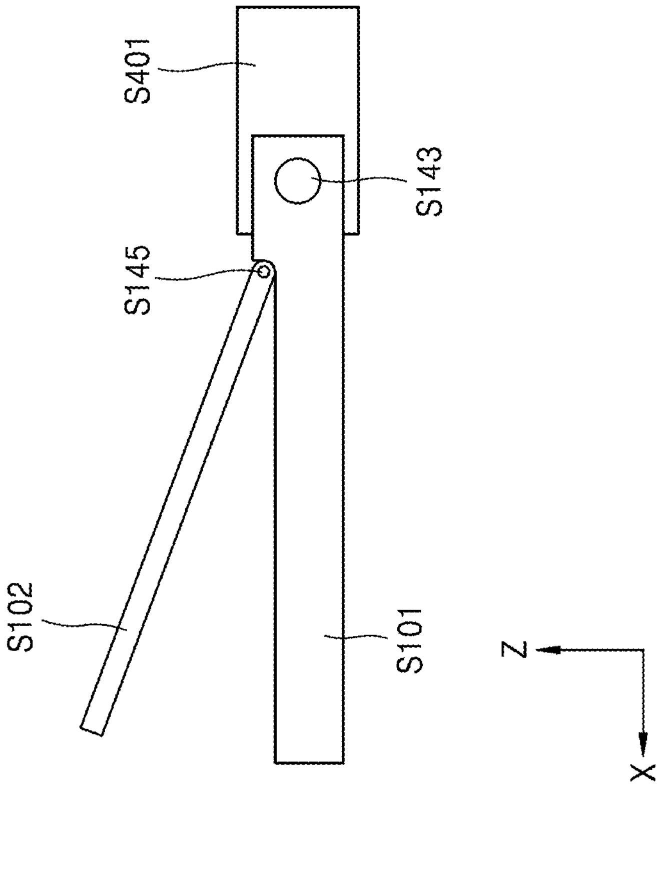

FIGS. 2A and 2B are diagrams illustrating a motion of the end tool when the anvil-centric function does not work, and FIGS. 3A to 5B are diagrams illustrating a motion of the end tool when the anvil-centric function works.

Referring to FIGS. 2A to 5B, a first jaw S101 may be axially coupled to a shaft, that is, the connection part S401, through a pitch rotation shaft S143. Also, a second jaw S102 may be axially coupled to the first jaw S101 through a second jaw rotation shaft S145.

In other words, the first jaw S101 may pitch-rotate about the pitch rotation shaft S143, and the second jaw S102 may rotate relative to the first jaw S101 about the second jaw rotation shaft S145. That is, the second jaw S102 rotates about the second jaw rotation shaft S145 and may perform an opening or closing operation. Here, the second jaw rotation shaft S145 may be formed in the first jaw S101, and the second jaw rotation shaft S145 may be formed parallel to the pitch rotation shaft S143.

Hereinafter, for convenience of description, the second jaw rotation shaft and the pitch rotation shaft are described as being different axes. However, the concept of the present disclosure is not necessarily limited thereto, and the second jaw rotation shaft may be a rotation shaft that shares the same axis as the pitch rotation shaft.

Referring to FIGS. 2A and 2B, when the anvil-centric function does not work, as shown in FIG. 2B, during the closing operation of the jaw, the first jaw S101 stays in place and the second jaw S102 rotates in a direction toward the first jaw S101, so that the first jaw S101 and the second jaw S102 are closed.

Figure 3A:
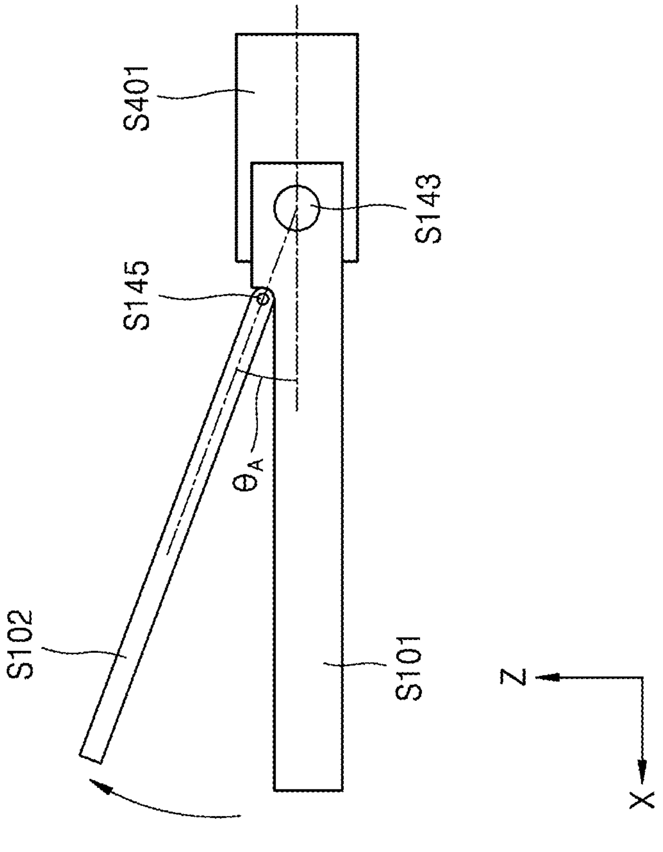
Figure 3B:
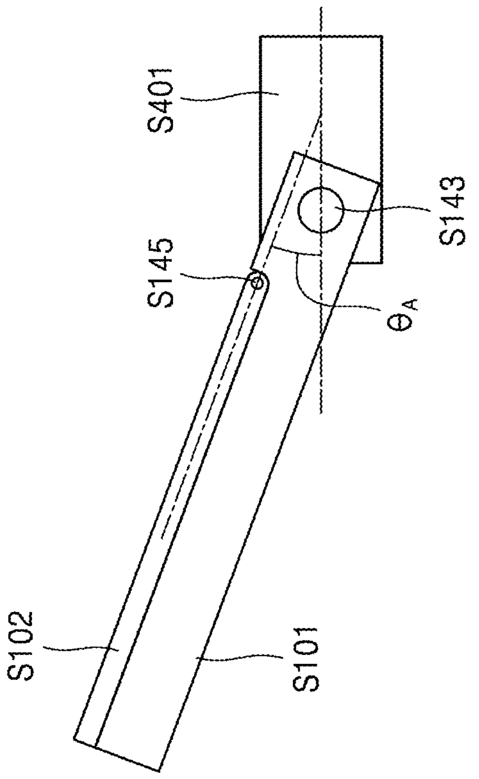

Meanwhile, referring to FIGS. 3A and 3B, when the anvil-centric function works, the first jaw S101 and the second jaw S102 may face each other and perform an opening or closing operation, but the first jaw S101 may rotate about the pitch rotation shaft S143 in a direction opposite to the rotation direction of the second jaw S102 in response to the second jaw S102 that rotates about the second jaw rotation shaft S145.

In other words, during the closing operation of the jaw, the first jaw S101 may rotate in a direction toward the second jaw S102, so that the first jaw S101 and the second jaw S102 are closed, and here, in response to the rotation of the second jaw S102, the first jaw S101 makes a pitch rotation in the opposite direction, thereby implementing a motion as if the second jaw S102 stays in place and the first jaw S101 rotates in a direction toward the second jaw S102.

From another perspective, during the opening or closing operation of the first jaw S101 and the second jaw S102, an angle formed by the second jaw S102 and the connection part S401 is maintained constant, and an angle formed by the first jaw S101 and the second jaw S102 may change as the first jaw S101 pitch-rotates.

In detail, as shown in FIG. 3A, when the first jaw S101 and the second jaw S102 are open and the angle formed between the second jaw S102 and the connection part S401 is $\theta_A$, the angle formed by the connection part S401 and the second jaw S102 may remain the same at $\theta_A$ even after the closing operation of the jaw.

In detail, the rotation shaft of the second jaw formed in the first jaw S101 moves in position as the first jaw S101 is pitch-rotated, so that the absolute coordinates of the second jaw S102 rotating through the second jaw rotation shaft S145 may not remain the same, but the angle formed by the connection part S401 and the second jaw S102 based on the connection part S401 may remain the same.

Meanwhile, when a basic state in which end tool manipulation by the manipulation part 200 is not applied to the end tool 100 according to the first embodiment of the present disclosure is considered a neutral state, a state in which the first jaw S101 and the second jaw S102 are open and the first jaw S101 is parallel to the connection part S401 may be set to the neutral state. The neutral state of the end tool 100 may be determined through initial setting of the pulley of the end tool, the pulley of the manipulation part, and the power transmission part.

As shown in FIGS. 3A and 3B, the state in which the first jaw S101 is parallel to the connection part S401 may be set to a neutral state, and in the neutral state, if the end tool 100 does not make a yaw or pitch motion and performs only the closing operation of the jaw, the end tool may not be parallel to the connection part S401 after the closing operation of the jaw. In other words, the end tool 100 may form a state forming a certain angle with the connection part S401, and may be pitch-rotated at the same angle as an angle formed by the second jaw S102 and the connection part S401 in the neutral state.

Figure 4A:
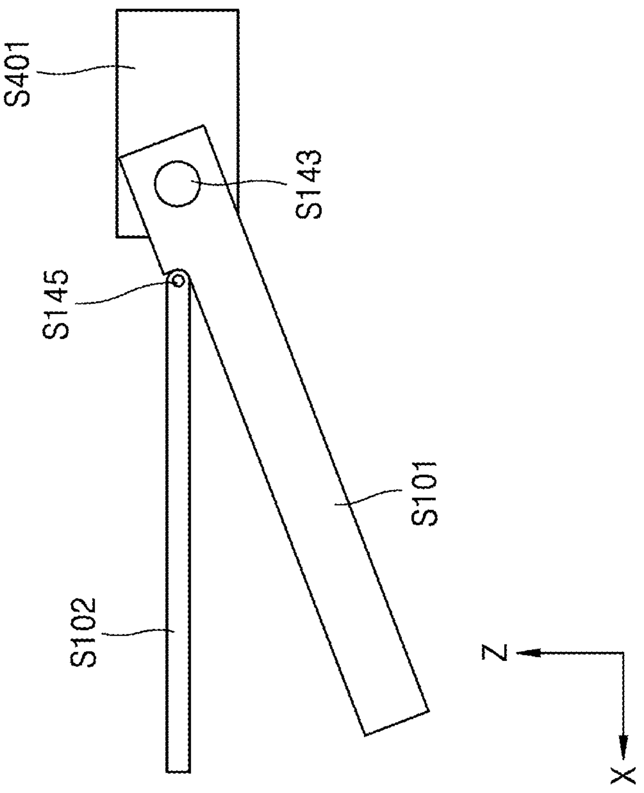
Figure 4B:
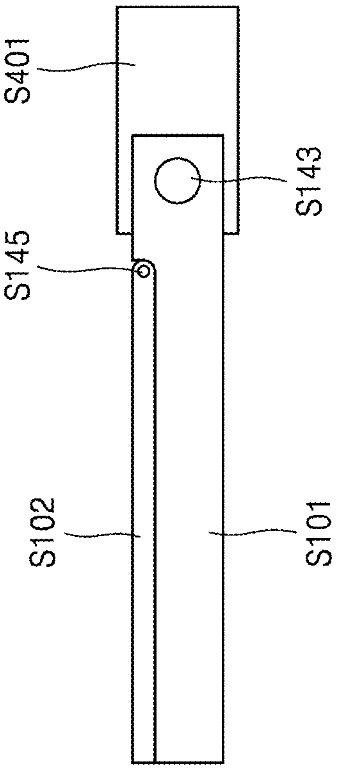

Meanwhile, as shown in FIGS. 4A and 4B, a state in which the first jaw S101 and the second jaw S102 are open and the second jaw S102 is parallel to the connection part S401 may be set to a neutral state.

In other words, the state in which the second jaw S102 is parallel to the connection part S401 may be set to a neutral state, and in the neutral state, if the end tool 100 does not perform a yaw or pitch motion and only performs a jaw closing operation, the end tool 100 may be parallel to the connection part S401 after the jaw closing operation. That is, in the neutral state, the first jaw S101 is pitch-rotated downward in the drawing with respect to the connection part S401, and after the closing operation, the first jaw S101 may be parallel to the connection part S401.

Hereinafter, a control method of the anvil-centric function to implement an anvil-centric motion by simulating the anvil-centric design is described.

The end tool 100 having an anvil-centric function and the surgical instrument 10 including the end tool may implement the aforementioned function by pitch-rotating the first jaw S101 in the opposite direction by the angle at which the second jaw S102 rotates. Through manipulation of the manipulation part 200, the stapling operation of the end tool and the closing operation of second jaw S102 may occur simultaneously. At this time, the first jaw S101 may be set to be pitch-rotated at the same time when the second jaw performs a closing operation through an actuator (not shown) of the manipulation part 200.

In detail, if the second jaw rotation shaft S145 is a rotation shaft that shares the same shaft as the pitch rotation shaft S143 of first jaw S101, the above function may be achieved by pitch-rotating the first jaw S101 by the same rotation amount as a rotation amount of the second jaw S102.

Meanwhile, if the second jaw rotation shaft S145 is spaced apart from the pitch rotation shaft S143 of first jaw S101, the rotation amount of first jaw S101 may not be the same as the rotation amount of the second jaw S102. For example, as shown in FIGS. 3A and 3B, when the second jaw S102 is connected to the proximal end side of the first jaw S101, a distance from the pitch rotation shaft S143 to the end portion of the second jaw S102 is longer than a distance from the second jaw rotation shaft S145 to the end portion of the second jaw S102, and thus, the pitch rotation amount of the first jaw S101 may be actually smaller than the rotation amount of the second jaw S102.

In other words, when the first jaw S101 rotates in response to the rotation of the second jaw S102, the first jaw S101 may pitch-rotate at the same rotation angle as the rotation angle of the second jaw S102 or may pitch-rotate at a rotation angle of a preset ratio with respect to the rotation angle of the second jaw S102.

Therefore, as described above, the anvil-centric function may be implemented by determining the pitch rotation amount suitable for the design of the end tool 100 by adjusting the setting of the actuator of the manipulation part 200.

Meanwhile, the end tool 100 according to the first embodiment of the present disclosure may include a first function of implementing an opening or closing operation of the first jaw S101 and the second jaw S102 by rotating the first jaw S101 about the pitch rotation shaft S143 in response to the second jaw S102 rotating about the second jaw rotation shaft S145 and a second function of implementing the opening or closing operation of the first jaw S101 and the second jaw S102 by rotating the second jaw S102 in a state in which the first jaw S101 is fixed, and the end tool 100 may be selected by one of the first function and the second function to be driven. In other words, the end tool 100 according to the first embodiment of the present disclosure may be operated by selecting the anvil-centric function described as the first function and a non-anvil-centric function described as the second function.

Figure 5A:
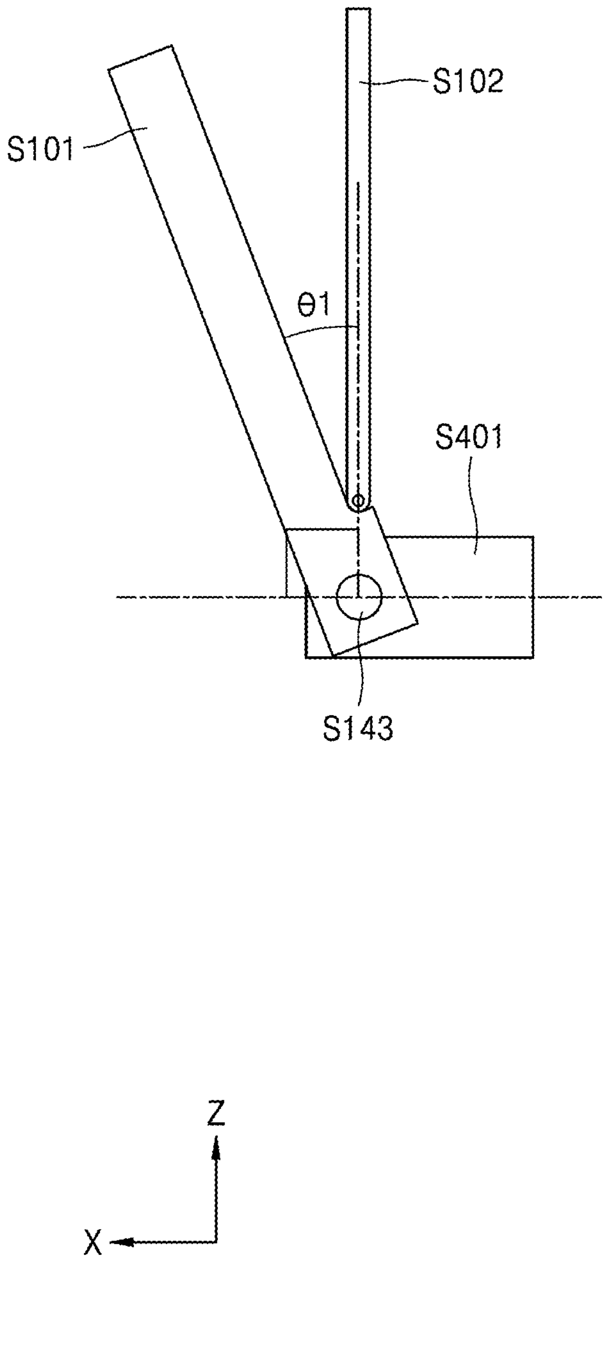
Figure 5B:
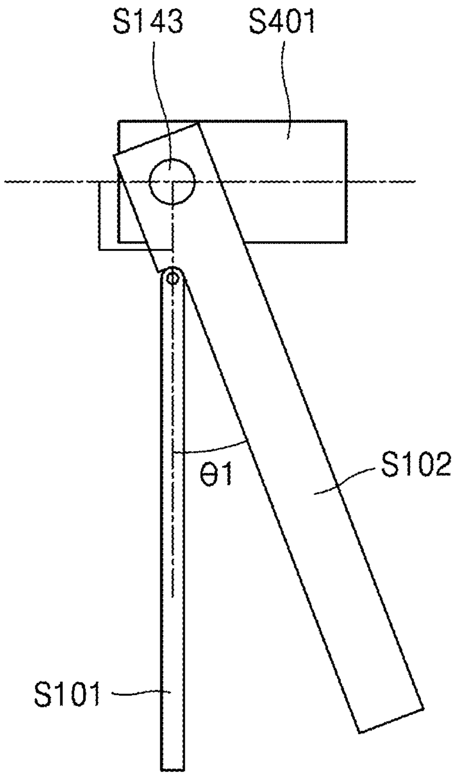

FIG. 5 is a diagram illustrating a rotation angle range of the first jaw S101 and the second jaw S102 in the end tool 100 in which the anvil-centric function is implemented.

When the end tool 100 pitch-rotates up and down based on the x-axis, which is an extension direction of the connection part S401, an upward rotation of the end tool 100 is described as rotating at a +angle and, conversely, a downward rotation is described as rotating at a −angle.

When the pitch rotation angle range of the end tool 100 is 180°, the end tool 100 rotates at an angle of ±90°. Without the anvil-centric function, the pitch rotation angle range is set based on first jaw S101, so the rotation angle of first jaw S101 may be ±90°.

Meanwhile, with the anvil-centric function, it may be convenient to set the pitch rotation angle range based on the second jaw S102, so the pitch rotation angle of the end tool 100 may be set based on the second jaw S102. That is, in order for the rotation angle of the end tool 100 to be ±900 based on the second jaw S102, it is necessary to set the pitch rotation angle range of the jaw S101 by considering an angle at which first jaw S101 and second jaw S102 are open.

For example, as shown in FIG. 5, if the angle between the first jaw S101 and the second jaw S102 during the opening operation of the jaw is $\theta_1$, the rotation angle range of the second jaw S102 may be +90° to −90° based on the extension direction (x-axis) of the connection part S401, and the rotation angle range of first jaw S101 may be $+90\text{-}\theta_1°$ to $-90\text{-}\theta_1°$ based on the extension direction (x-axis) of the connection part S401.

For example, if the angle between the first jaw S101 and the second jaw S102 is 15°, the first jaw S101 may pitch-rotate within the range of +75° to −105°. That is, the first jaw S101, which pitch-rotates based on the pitch rotation shaft S143, may pitch-rotate within a range of 180°.

By correcting the rotation angle range of the jaw in this manner, the end tool 100 with the first jaw S101 and the second jaw S102 in a closed state may be pitch-rotated in the ±90° range. In other words, even though the rotation range of first jaw S101 is asymmetric, the rotation range of second jaw S102 is symmetrical, so the rotation range of the end tool 100 that is closed with respect to the second jaw S102 may be symmetrical.

Hereinafter, a joint structure of the end tool is described.

Figure 6:
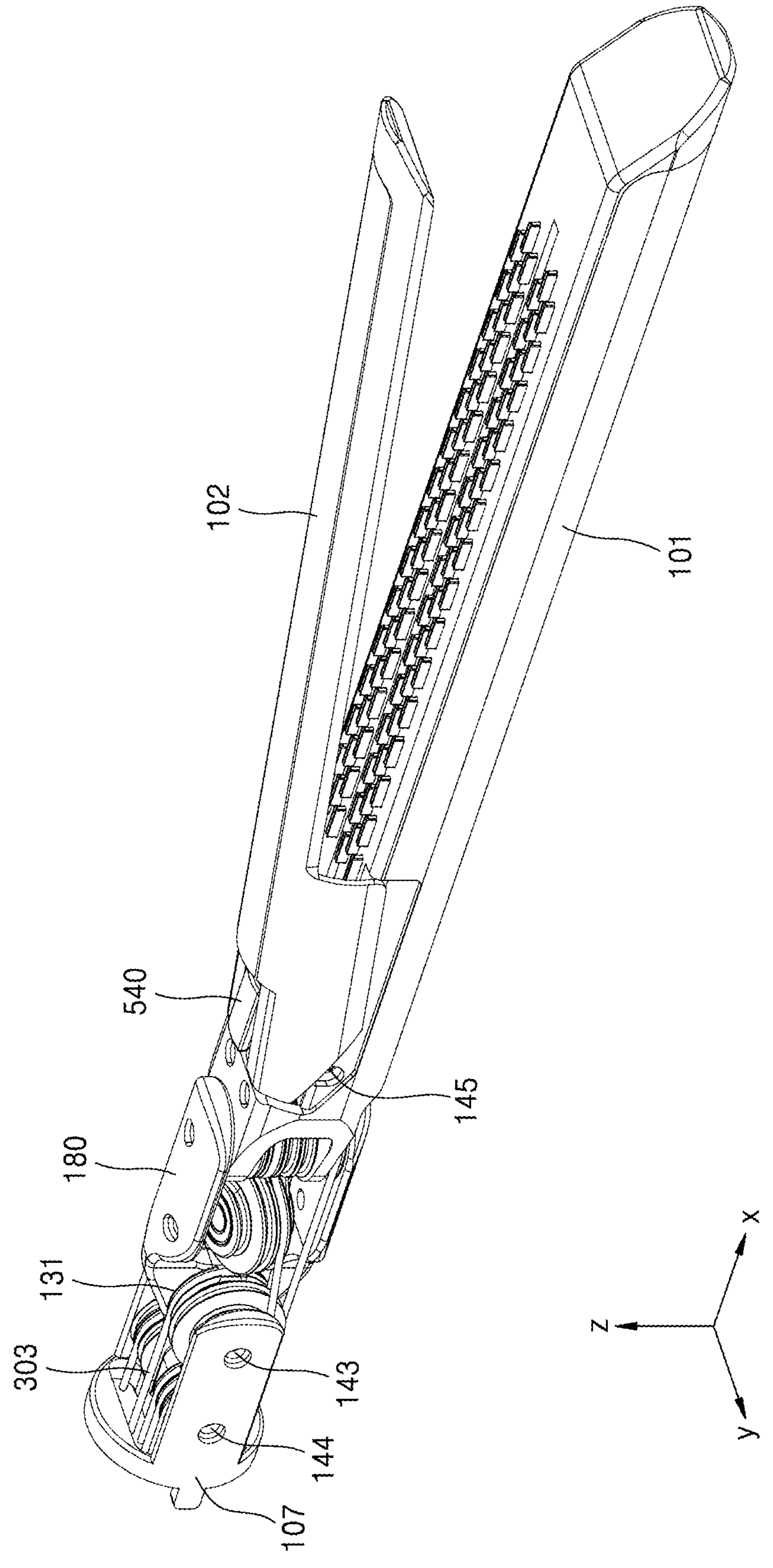
FIG. 6 is a perspective view showing the end tool of FIG. 1.
Figure 7:
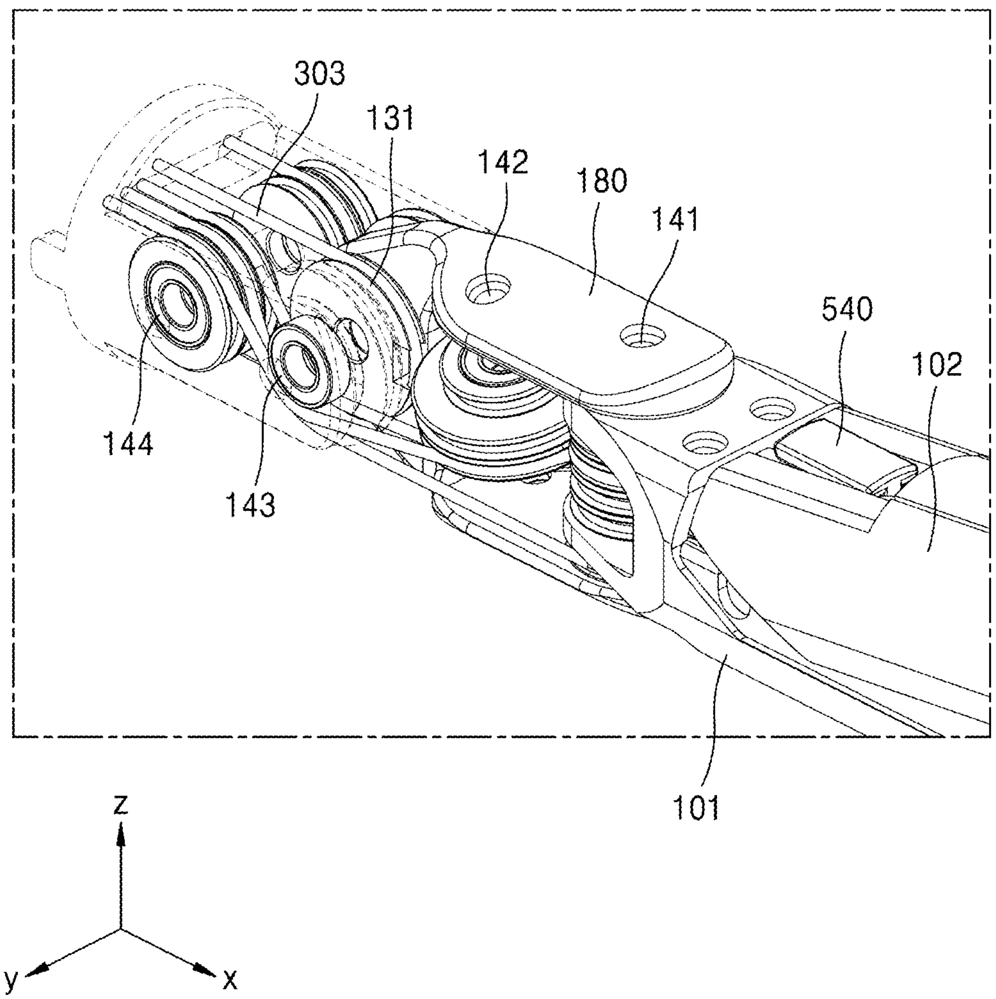
FIG. 7 is an enlarged perspective view showing a pitch pulley part of the end tool of FIG. 6.
Figure 8:
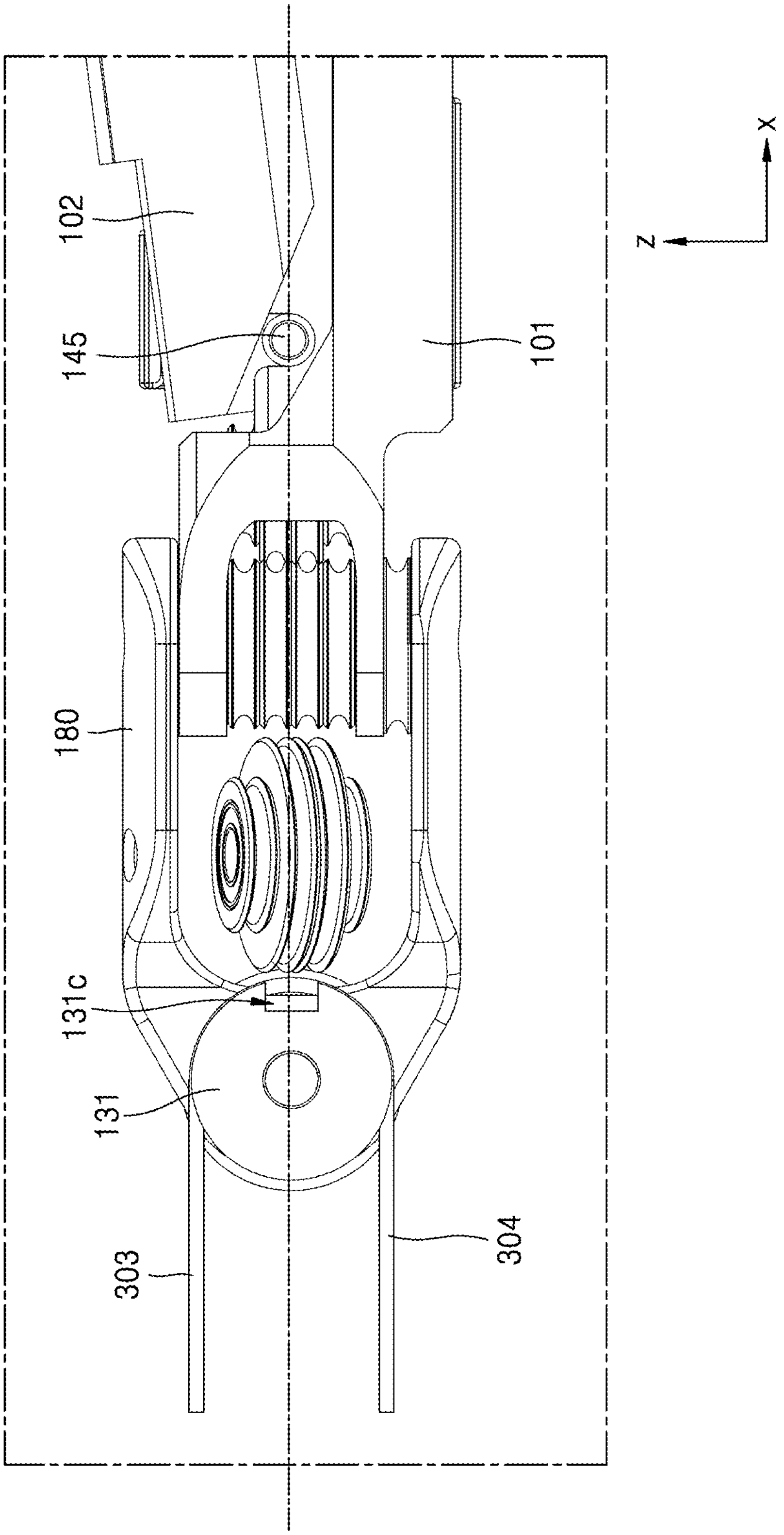
FIG. 8 is a side view showing the end tool without a second end tool hub of FIG. 7.
Figure 9:
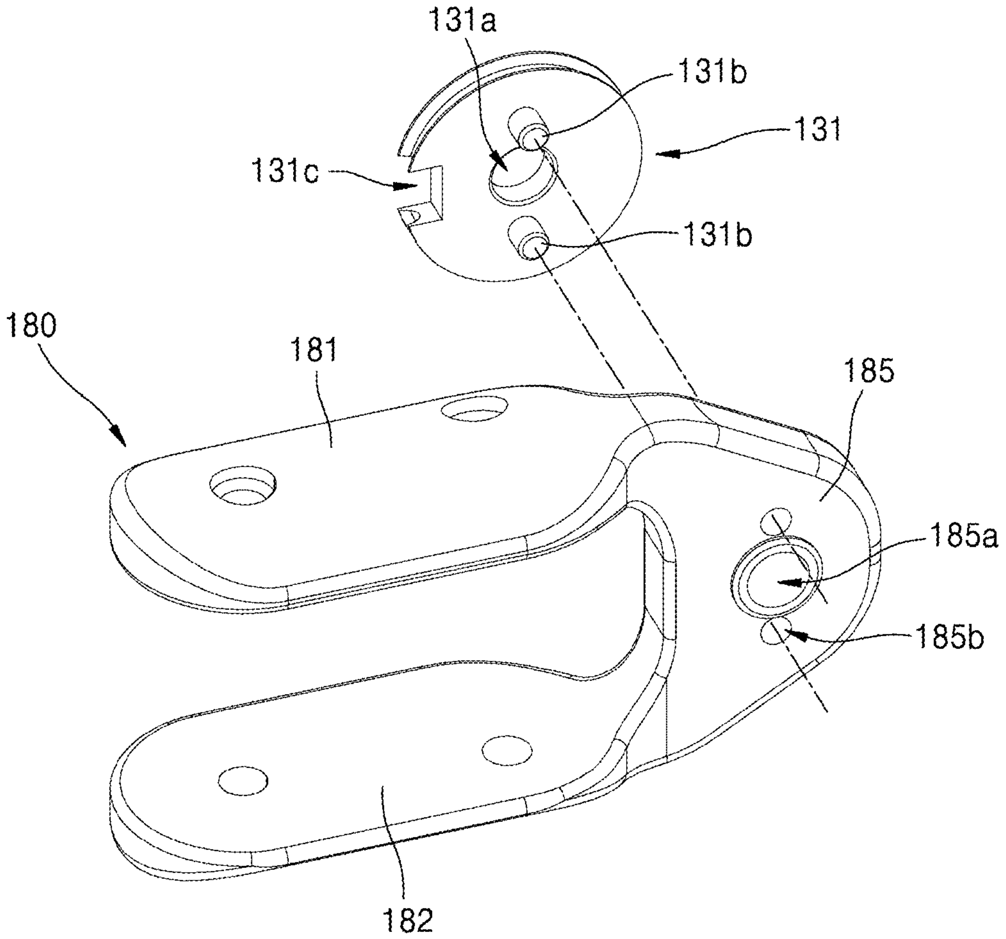
FIG. 9 is a perspective view showing a first end tool hub and a pitch pulley of FIG. 7.
Figure 10:
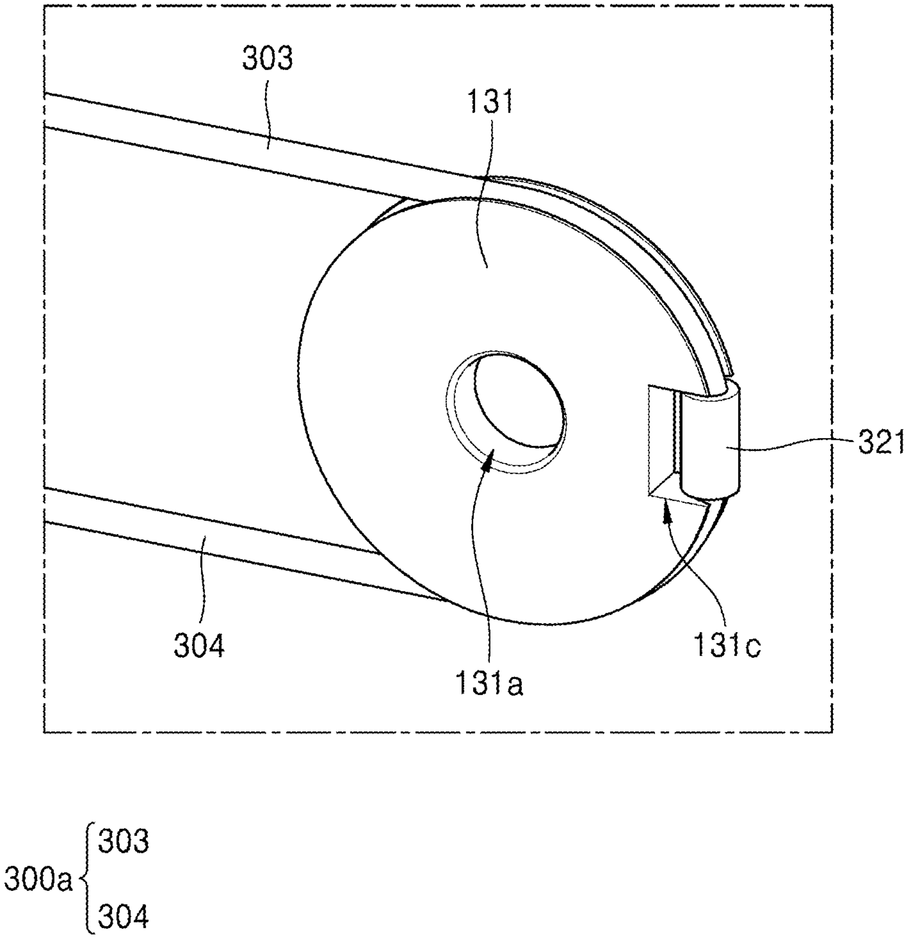
FIG. 10 is a perspective view showing a pitch wire combined with the pitch pulley of FIG. 7.
Figure 11:
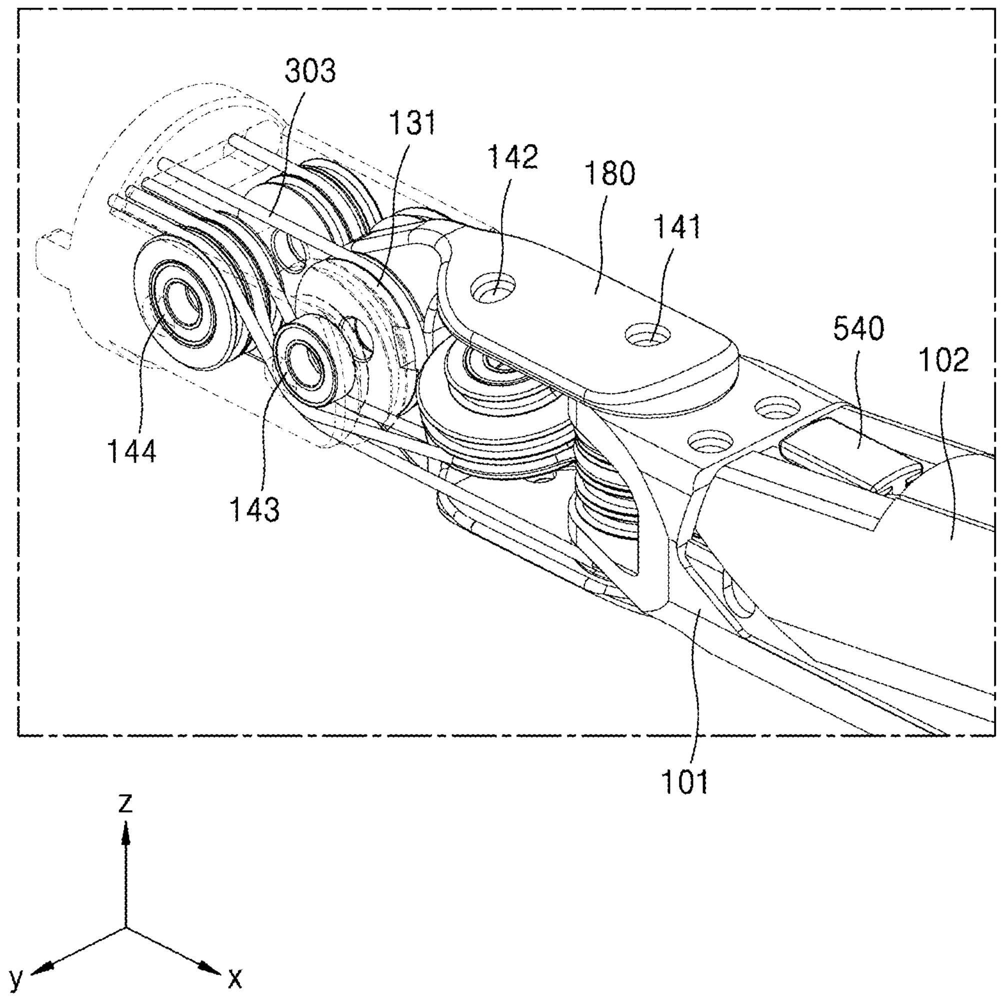
FIG. 11 is an enlarged perspective view showing the pitch pulley with a fastening member adjusted in position in the end tool of FIG. 6.
Figure 12:
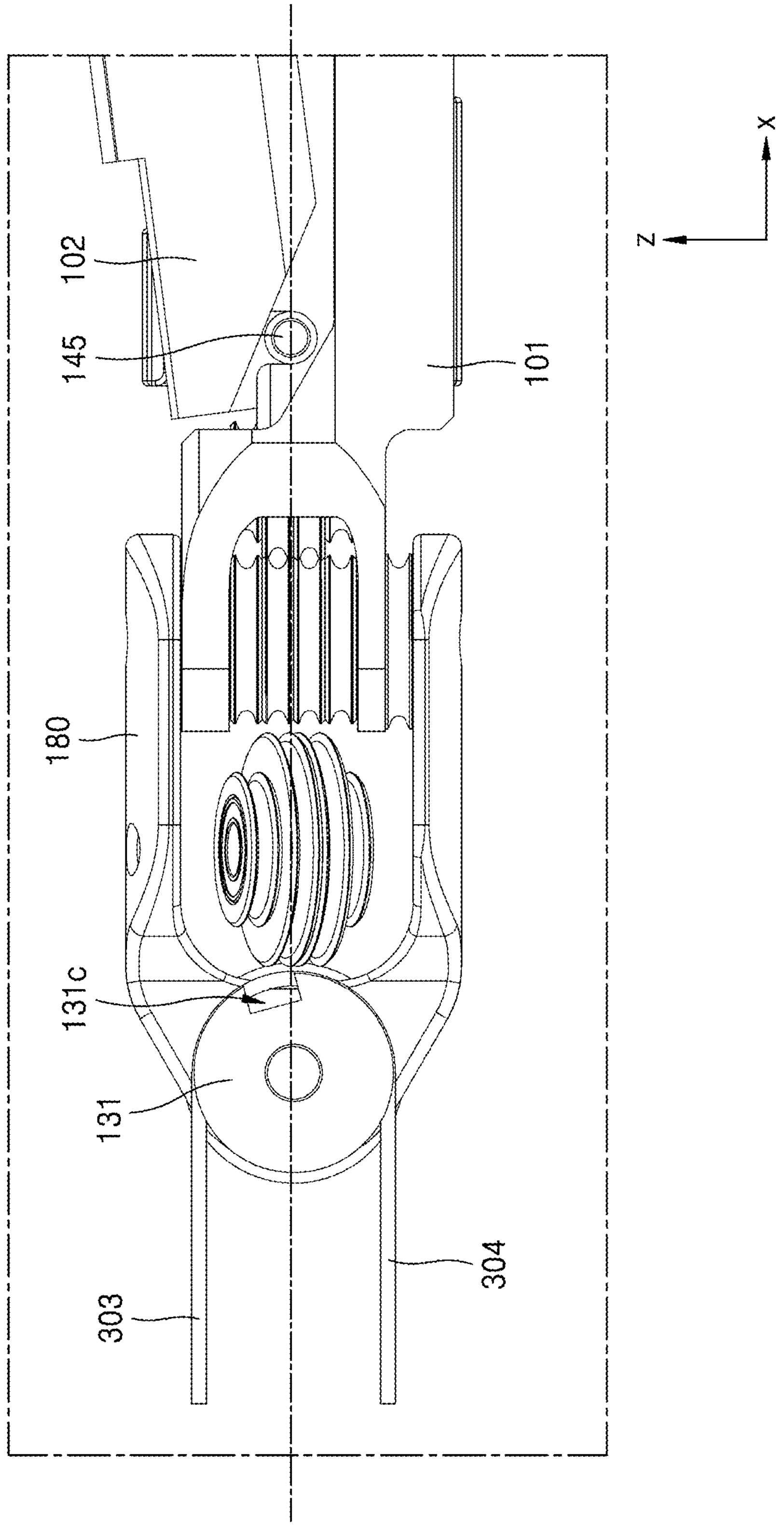
FIG. 12 is a side view showing the end tool without the second end tool hub of FIG. 11.

FIG. 6 is a perspective view showing the end tool of FIG. 1. FIG. 7 is an enlarged perspective view showing a pitch pulley part of the end tool of FIG. 6. FIG. 8 is a side view showing the end tool without a second end tool hub of FIG. 7. FIG. 9 is a perspective view showing a first end tool hub and a pitch pulley of FIG. 7. FIG. 10 is a perspective view showing a pitch wire combined with the pitch pulley of FIG. 7. FIG. 11 is an enlarged perspective view showing the pitch pulley with a fastening member adjusted in position in the end tool of FIG. 6. FIG. 12 is a side view showing the end tool without the second end tool hub of FIG. 11.

Referring to FIGS. 6 to 12, the end tool according to the first embodiment of the present disclosure may include the first jaw, the second jaw, and the end tool hub.

The jaw may perform various functions, for example, a grip operation, and as a specific example, the jaw may include a pair of jaws, that is, the first jaw 101 and the second jaw 102. Here, the first jaw 101 and the second jaw 102, respectively, or a component encompassing the first jaw 101 and the second jaw 102 may be referred to as the jaw 103.

The first jaw 101 and the second jaw 102 may be arranged to face each other, may move toward each other and away from each other, and may be formed to rotate about one axis, for example.

The first jaw 101 may be partially accommodated in a first end tool hub 180 to described below and may yaw-rotate about a rotation shaft. In addition, the first jaw 101 may perform pitch rotation about the pitch rotation shaft 143 to be described below.

Meanwhile, an second jaw rotation shaft 145, which is a rotation center of the second jaw 102, may be formed to be adjacent to the proximal end of the first jaw 101. Here, second jaw rotation shaft 145 may be formed parallel to the pitch rotation shaft 143.

Accordingly, a virtual plane including a rotation range of the second jaw 102 and a virtual plane including a pitch rotation range of the first jaw 101 may be the same.

The end tool 100 may include one or more members, for example, a joint member, connecting the jaw 103 to the connection part 400. In addition, as an optional embodiment, the end tool 100 may include an end tool hub.

The end tool hub may be located to connect the end tool 100 to the straight part 401 of the connection part 400. From another perspective, the end tool hub may be a member that connects the connection part 400 to the first jaw 101 and the second jaw 102.

The end tool hub may include a first end tool hub 180 and a second end tool hub 107.

Here, the first end tool hub 180 may be formed to accommodate at least a portion of the first jaw 101 therein.

Meanwhile, the second end tool hub 107 may be axially coupled to the first end tool hub 180 and may be rotatable relative to the first end tool hub 180. Also, the first end tool hub 180 and the second end tool hub 107 may be axially coupled through the pitch rotation shaft 143. Details of the second end tool hub 107 are described below.

The first end tool hub 180 may include a pair of jaw pulley coupling parts 181 and 182 and a pitch pulley part 185.

In detail, the pair of jaw pulley coupling parts 181 and 182 are formed to face each other, so that a plurality of pulleys may be accommodated therein. In addition, a through-hole is formed in each of the pulley coupling parts 181 and 182, so that the rotation shaft 141 may pass through the jaw pulley coupling parts 181 and 182 and the pulley to axially couple them.

The pair of jaw pulley coupling parts 181 and 182 may be connected by the pitch pulley part 185. That is, the pair of jaw pulley coupling parts 181 and 182 parallel to each other are coupled by the pitch pulley part 185 formed in a direction approximately perpendicular to the pair of jaw pulley coupling parts 181 and 182, so that the pair of jaw pulley coupling parts 181 and 182 and the pitch pulley part 185 form an approximately "C" shape and a plurality of pulleys are accommodated therein.

From another perspective, the pair of jaw pulley coupling parts 181 and 182 may be formed to extend in the X-axis direction from both end portions of the pitch pulley part 185 elongated in the Z-axis direction.

Also, a pitch pulley 131, around which a wire 303 and a wire 304, which are a pitch wire, may be wound, may be coupled to the pitch pulley part 185. Alternatively, the pitch pulley 131 may not be a member that rotates about a predetermined axis, like a pulley in the original sense, but may be formed to be fixed as a portion of the first end tool hub 180, and as a wire is wound around the circumference of the pitch pulley 131, the pitch pulley 131 may perform the function of a pulley partially similarly. Here, the pitch pulley part 185 may be formed on the XZ plane. In addition, a through-hole through which the rotation shaft 143 may be inserted may be formed in the pitch pulley part 185.

The first end tool hub 180 may have the rotation shaft 141 and the rotation shaft 142 inserted therethrough and may also accommodate at least a portion of the pulley axially coupled to the rotation shaft 141 therein. In addition, the first end tool hub 180 may accommodate at least a portion of the pulley axially coupled to the rotation shaft 142 therein.

Here, the rotation shaft 142 may be located side by side with the rotation shaft 141 but may not be parallel to the rotation shaft 141. That is, the rotation shaft 141 may be located in the Z-axis direction in the drawing, but the rotation shaft 142 may be located obliquely at a certain angle with respect to the Z-axis.

Meanwhile, the pitch pulley 131 that functions as an end tool pitch pulley may be formed at one end portion of the first end tool hub 180. The pitch pulley 131 may be formed as one body with the first end tool hub 180. That is, a disc-shaped pulley may be formed at one end portion of the first end tool hub 180, and a groove into which a wire may be wound may be formed on an outer peripheral surface of the pulley. Alternatively, the pitch pulley 131 may be formed as a separate member from the first end tool hub 180 and may be coupled to the first end tool hub 180. A pitch wire, to be described below, is coupled to the pitch pulley 131, which functions as an end tool pitch pulley, and the pitch pulley 131 rotates about the rotation shaft 143 to perform a pitch operation.

Referring to FIG. 9, the pitch pulley 131 may include a coupling part **131*b* that fixedly couples the pitch pulley 131 to the first end tool hub 180. Here, the coupling part 131*b* may be a protrusion formed to protrude from a surface of the pitch pulley 131 in contact with the first end tool hub 180. Also, the coupling part 131*b* may be fitted into a coupling hole 185*b* formed in the first end tool hub 180 to fix the pitch pulley 131 to the first end tool hub 180**.

Here, the coupling part **131*b*** may be formed in plurality, may not be limited to the shape and number shown in the drawings, and may be formed in various shapes and numbers.

In addition, although not shown in the drawing, a coupling part protruding from the first end tool hub 180 may be formed, a coupling hole may be formed in the pitch pulley 131, and the coupling part and the coupling hole may be coupled to connect the pitch pulley 131 to the first end tool hub 180.

In this manner, the first end tool hub 180 may be coupled to the pitch pulley 131 by the coupling part **131*b* and may rotate as one body with the pitch pulley 131 when the pitch pulley 131** rotates.

Meanwhile, the pitch pulley 131 may include a fastening recess **131*c*. The fastening recess 131*c* may be a portion to which a fastening member 321 of a pitch wire 300*a* to be described below is coupled. The fastening recess 131*c* may be a portion depressed by a certain depth from the edge of the pitch pulley 131, which is disk-shaped, toward the center of the pitch pulley 131. From another perspective, the fastening recess 131*c* may be a space provided so that the fastening member 321 greater than the thickness of the pitch wire 300*a* wound around the pitch pulley 131 may be stably fastened to the pitch pulley 131**.

Meanwhile, the end tool hub may include a portion of the pitch wire **300*a*. Here, at least a portion of the pitch wire 300*a* may be wound around the pitch pulley 131 to transmit driving force to the pitch pulley 131. In detail, a portion of the pitch wire 300*a* may be wound around the pitch pulley 131** of the end tool hub, and another portion may be connected to the manipulation part through a connection part.

In addition, the pitch wire **300*a* may further include the fastening member 321. The fastening member 321 may be coupled to the pitch wire 300*a* to couple the pitch pulley 131 to the pitch wire 300*a***.

Here, the fastening member 321 may have various shapes as needed, such as a ball shape or a tube shape.

A coupling relationship between the wires, the fastening member, and each pulley is described in detail as follows.

First, the wire 303 and wire 304, which are the pitch wire **300*a*, may be a single wire. After the fastening member 321 is inserted into a midpoint of the pitch wire 300*a*, which is a single wire, the fastening member 321 may be crimped to be fixed. Here, both strands of the pitch wire 300*a* based on the fastening member 321 may be referred to as the wire 303 and the wire 304**, respectively.

In other words, the pitch wire **300*a* may be formed as a single wire, and the fastening member 321 may be fastened to a portion of the pitch wire 300*a***.

Alternatively, the wires 303 and 304, which are the pitch wire **300*a*, may be formed as separate wires, and the wires 303 and 304 may be connected by the fastening member 321**.

Also, by coupling the fastening member 321 to the pitch pulley 131, the wire 303 and the wire 304 may be fixedly coupled to the pitch pulley 131. As a result, the pitch pulley 131 may rotate as the wire 303 and the wire 304 are pulled and released.

Also, the end portions of the wire 303 and the wire 304 opposite to the portion to which the fastening member 321 is fastened may be coupled to a pulley of the manipulation part. Also, when the pulley of the manipulation part rotates by a motor or human force, the wire 303 and the wire 304 are pulled and released, allowing the pitch pulley 131 of the end tool 100 to rotate.

Meanwhile, the second end tool hub 107 may be axially coupled to the first end tool hub 180 and may be rotatable relative to the first end tool hub 180. Also, the first end tool hub 180 and the second end tool hub 107 may be axially coupled through the pitch rotation shaft 143.

The second end tool hub 107 may form a disc-shaped body on one side coupled to the connection part 400 and may be formed as a portion extending from the body toward the first end tool hub 180.

Also, the rotation shaft 143 and a rotation shaft 144 to described below may be inserted through the extension part extending toward the first end tool hub 180, and the second end tool hub 107 and the first end tool hub 180 (and pitch pulley 131) may be axially coupled by the rotation shaft 143. Accordingly, the first end tool hub 180 and the pitch pulley 131 may be formed to be rotatable with respect to the second end tool hub 107 about the rotation shaft 143.

In addition, the second end tool hub 107 may accommodate at least a portion of a pulley axially coupled to the rotation shaft 143 therein. In addition, the second end tool hub 107 may accommodate at least a portion of a pulley axially coupled to the rotation shaft 144 therein.

The rotation shaft 143 may function as a pitch rotation shaft, and the rotation shaft 144 may function as an auxiliary pulley rotation shaft.

The auxiliary pulley rotation shaft 144 may be located parallel to the pitch rotation shaft 143 and adjacent to the pitch rotation shaft 143.

Also, the second end tool hub 107 may further include a pitch auxiliary pulley 132 rotating about the auxiliary pulley rotation shaft 144. Details thereof are described below.

Hereinafter, a structure for making a rotation range of the jaw asymmetrical is described.

Figure 13:
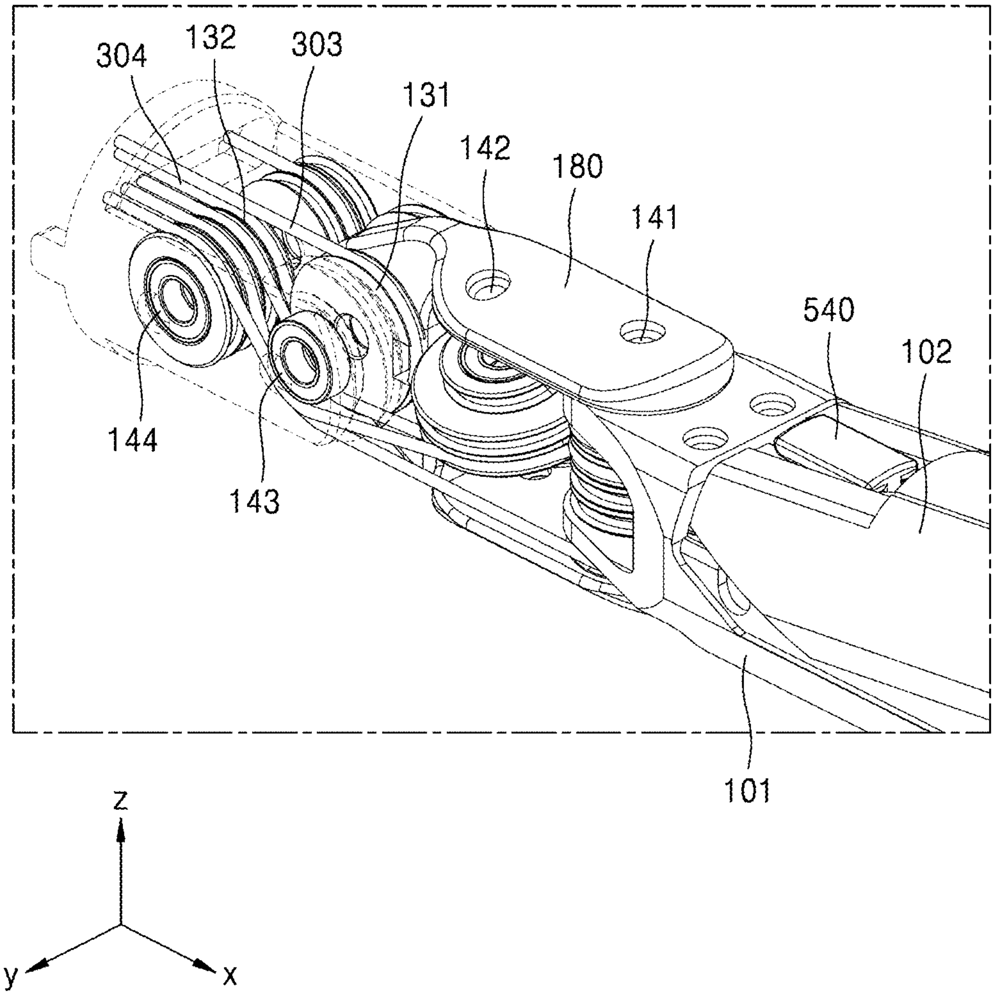
FIG. 13 is an enlarged perspective view showing an end tool according to a modified example of the first embodiment of the present disclosure.

Referring to FIGS. 12 and 13, the first end tool hub 180 and the second end tool hub 107 may be axially coupled through the pitch rotation shaft 143, and the pitch rotation shaft 143 may be inserted through the center of the pitch pulley 131. As described above, the fastening recess 131*c* to which the fastening member 321 is coupled may be formed in the pitch pulley 131, and the pitch pulley 131 coupled to the fastening member 321 may rotate as the pitch wire 300*a* is pulled and released.

As shown in FIG. 8, when the fastening recess 131*c* is located on the X-axis, which is an extension direction of the connection part 400, that is, when an imaginary line connecting the fastening recess 131*c* to the center of the pitch pulley 131 is parallel to the X-axis, the pitch pulley 131 may rotate ±90°.

In detail, as the pitch pulley 131 rotates, a position of the fastening recess 131*c* may change, and the pitch pulley 131 may rotate so that the fastening recess 131*c* is located at the top of the pitch pulley 131 or may rotate so that the fastening recess 131*c* is located at the bottom of the pitch pulley 131.

That is, when both strands of the pitch wire 300*a* are arranged in parallel and wound around the pitch pulley 131, the pitch pulley 131 may rotate up to a contact point at which the pitch pulley 131 meets the pitch wire 300*a*.

Therefore, the pitch pulley 131 may rotate in the range of +90° to −90° with respect to the X-axis. Also, the first end tool hub 180 coupled to the pitch pulley 131 may pitch-rotate about the pitch rotation shaft 143, and the first jaw 101 connected to the first end tool hub 180 may pitch-rotate about the pitch rotation shaft 143. That is, the first jaw 101 may rotate in the range of +90° to −90° with respect to the X-axis, which is the extension direction of the connection part 400.

As described in FIG. 5, the rotation angle range of first jaw 101 may be suitable in the case in which there is no anvil-centric function. That is, because the pitch rotation angle range is set based on the first jaw 101, it may be appropriate for the rotation angle of the first jaw 101 to be ±90θ.

However, in the case of having the anvil-centric function, it may be convenient to set the pitch rotation angle range based on the second jaw 102, and thus the pitch rotation angle of the end tool 100 may be set based on the second jaw 102. That is, in order for the rotation angle of the end tool 100 to be ±90° based on the second jaw 102, it is necessary to set the pitch rotation angle range of the first jaw 101 by considering the angle at which the first jaw 101 and the second jaw 102 are open.

In other words, the rotation angle range of the second jaw 102 may become ±90° by asymmetrically correcting the rotation angle range of the first jaw 101.

Referring to FIGS. 11 and 12, when the first jaw 101 is in a neutral state parallel to the extension part, the pitch pulley 131 may have been rotated to some extent. In detail, an imaginary line connecting the center of the pitch pulley 131 and the fastening recess 131*c* may not be parallel to the extension direction (X-axis) of the connection part 400. That is, the imaginary line connecting the center of the pitch pulley 131 and the fastening recess 131*c* may form an angle of 0° to +90° with the extension direction (X-axis) of the connection part 400. Also, the state of the pitch pulley 131 may be described as offset.

Here, the state in which the pitch pulley 131 has already rotated in the neutral state may be made by adjusting it at the stage of coupling the pitch pulley 131 and the first end tool hub 180 or may be made by changing the position of the fastening recess 131*c* when manufacturing the pitch pulley 131.

As shown in FIG. 12, when the fastening recess 131*c* is +rotated relative to the X-axis, a +rotation angle range may be reduced, and conversely, a −rotation angle range may be expanded.

In other words, the rotation angle range of the pitch pulley 131 may be $+90-\theta_1°$ to $-90-\theta_1°$. Here, $\theta_1$ may be an angle between the first jaw 101 and the second jaw 102 during the opening operation of the jaw.

In this manner, by adjusting the position of the fastening recess 131*c*, the position at which the fastening member 321 is fixed to the pitch pulley 131 may be adjusted, and as a result, the pitch rotation angle range of the first jaw 101 may be adjusted by adjusting the rotation angle range of the pitch pulley 131.

When the rotation angle range of the jaw is corrected in this manner, even though the rotation range of the first jaw 101 is asymmetrical, the rotation range of the second jaw 102 is symmetrical, so the rotation range of the end tool 100 closed based on the second jaw 102 may be symmetrical. That is, the end tool 100 in which the first jaw 101 and the second jaw 102 are closed may be pitch-rotated in a range of ±90°. The convenience and usability of operating the end tool 100 may be improved.

Hereinafter, a structure for expanding the range of the pitch rotation angle of the end tool 100 is described.

Figure 14:
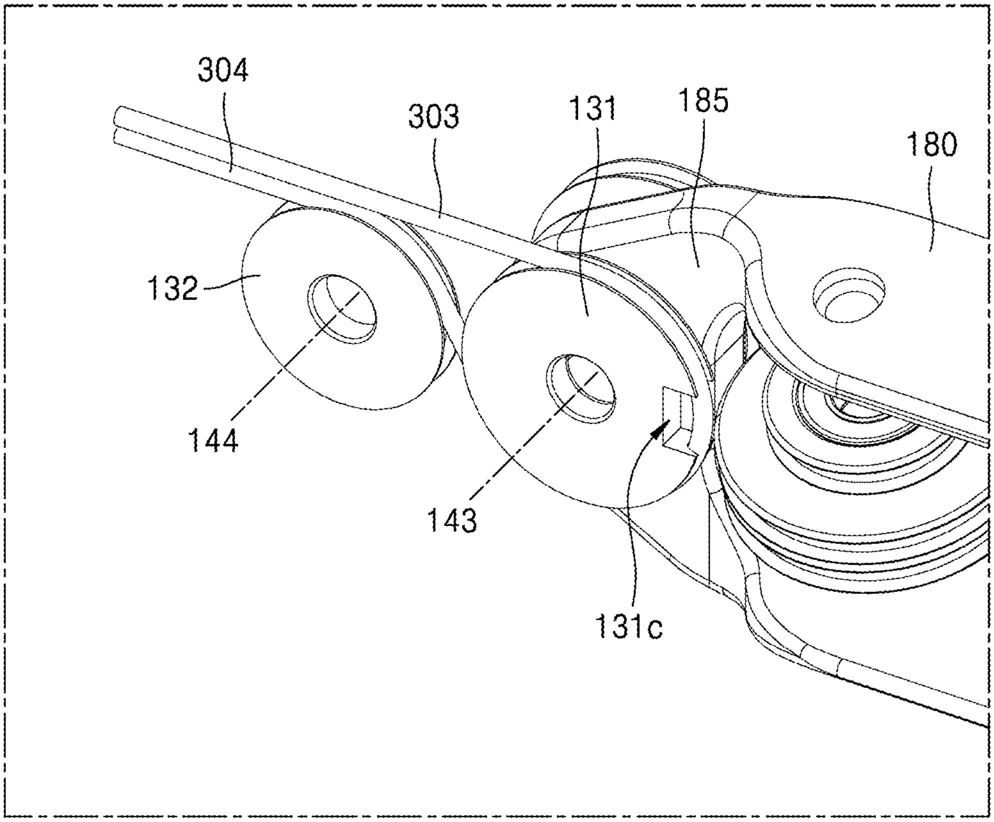
FIG. 14 is an enlarged perspective view showing the end tool without the second end tool hub of FIG. 13.

FIG. 13 is an enlarged perspective view showing the end tool 100 according to a modified example of the first embodiment of the present disclosure, and FIG. 14 is an enlarged perspective view showing the end tool 100 without the second end tool hub 107 of FIG. 13.

Referring to FIGS. 13 and 14, the end tool hub may include the auxiliary pulley rotation shaft 144 and the pitch auxiliary pulley 132.

The auxiliary pulley rotation shaft 144 may be formed in the second end tool hub 107. The auxiliary pulley rotation shaft 144 may be parallel to the pitch rotation shaft 143 and adjacent to the pitch rotation shaft 143.

Also, the auxiliary pulley rotation shaft 144 may be inserted through the center of the pitch auxiliary pulley 132. Also, the pitch auxiliary pulley 132 may rotate about the auxiliary pulley rotation shaft 144. In addition, the pitch auxiliary pulley 132 may be located adjacent to the pitch pulley 131.

In addition, both strands of the pitch wire 300*a* wound around the pitch pulley 131 and extending to the connection part 400 may be located on the same side with respect to the auxiliary pulley rotation shaft 144.

In detail, the wire 303, which is one strand of the pitch wire 300*a*, may be connected by winding an upper portion of the pitch pulley 131 in the drawing and the wire 304, which is the other strand of the pitch wire 300*a*, may be connected by winding a lower portion of the pitch pulley 131, and the wire 304 may be partially wound around the pitch auxiliary pulley 132 to pass.

A diameter of the pitch auxiliary pulley 132 may be smaller than a diameter of the pitch pulley 131. Therefore, even though the wire 304 is wound around the pitch auxiliary pulley 132 to pass, the wire 304 may be easily placed on the same side as the wire 303.

Meanwhile, the pitch wire 300*a* may be located on a common internal tangent line of the pitch pulley 131 and the pitch auxiliary pulley 132, the rotation angle of the pitch pulley 131 is expanded by the pitch auxiliary pulley 132, and the rotation angle range of the second jaw 102 may be expanded by an additional angle set by the pitch auxiliary pulley 132.

In detail, the wire 304, which is one strand of the pitch wire 300*a*, may be located on the common internal tangent line of the pitch pulley 131 and the pitch auxiliary pulley 132. That is, a path of the wire 304 may be changed by the pitch auxiliary pulley 132.

Accordingly, a length of the pitch wire 300*a* wound around the pitch pulley 131 may increase. That is, the position of the contact point between the wire 304, which is the pitch wire 300*a*, and the pitch pulley 131 is changed and the pitch pulley 131 may rotate to the contact point in contact with the pitch wire 300*a*, so the rotation range of the pitch pulley may be eventually expanded.

For example, the rotation angle range of the pitch pulley 131 may be expanded by an additional 600 compared to the existing range. That is, the rotatable angle range of the pitch pulley 131 may be 240°.

As shown in FIG. 14, when the pitch pulley 131 is not in an offset state, that is, when the fastening recess 131*c* is located in the extension direction (X-axis) of the connection part 400, the pitch pulley 131 may be able to rotate by +90° to −150°.

In addition, as described above, the rotation angle range of the pitch pulley 131 may be appropriately adjusted by offsetting the pitch pulley 131. For example, the pitch pulley 131 may be able to rotate by +120° to −120°.

In addition, the rotation angle range of the end tool 100 according to a modified example of the first embodiment of the present disclosure may be adjusted in combination with the anvil-centric function. For example, when the anvil-centric function works, the second jaw 102 may rotate in the range of +120° to −120° and the first jaw 101 may rotate in the range of $+120\text{-}\theta_1°$ to $-120\text{-}\theta_1°$.

Therefore, the end tool 100 according to a modified example of the first embodiment of the present disclosure may improve the convenience and usability of the end tool manipulation.

Meanwhile, the joint member of the end tool 100 connecting the jaw and the connection part 400 may be formed in various shapes.

For example, the rotation shaft at which the first end tool hub 180 and the first jaw 101 are coupled may function as the pitch rotation shaft 143. That is, the first end tool hub 180 and the first jaw 101 may be axially coupled through the pitch rotation shaft 143. Also, the end tool hub may include the pitch pulley 131 formed to rotatable about the pitch rotation shaft 143 and the pitch wire 300*a* at least partially wound around the pitch pulley 131 and transmitting driving force to the pitch pulley 131 300*a*.

In other words, the pitch rotation shaft 143, which is a pitch rotation center of the first jaw 101, may be formed close to the first jaw 101 or close to the connection part 400. However, regardless of the position of the pitch rotation shaft 143, the second jaw rotation shaft 145 may be located parallel to the pitch rotation shaft 143 and may be designed so that the anvil-centric function works. In addition, the rotation angle range of the first jaw 101 may be adjusted asymmetrically through the offset of the pitch pulley 131.

So far, the present disclosure has been examined with a focus on preferred embodiments. A person skilled in the art to which the present disclosure pertains will understand that the present disclosure may be implemented in a modified form without departing from the essential characteristics of the present disclosure. Therefore, the disclosed embodiments should be considered from an illustrative rather than a limiting perspective. The scope of the present disclosure is indicated in the claims rather than the foregoing description, and all differences within the equivalent scope should be construed as being included in the present disclosure.

According to the present disclosure, the end tool and surgical instrument may improve convenience of use by simulating the anvil-centric motion without having an anvil-centric design.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. An end tool of a surgical instrument, which is coupled to one end of a connection part of an external device, the end tool comprising:

a first jaw rotatable about a pitch rotation shaft; and a second jaw relatively rotatable with respect to the first jaw about a second jaw rotation shaft disposed in the first jaw parallel to the pitch rotation shaft, wherein the first jaw and the second jaw are opposed to each other and perform an opening or closing operation, and the first jaw rotates about the pitch rotation shaft but rotates in a direction opposite to a rotation direction of the second jaw in response to the second jaw rotating about the second jaw rotation shaft.

2. The end tool of claim 1, wherein, during the opening or closing operation of the first jaw and the second jaw, an angle formed by the second jaw and the connection part is maintained constant, and an angle formed by the first jaw and the second jaw changes as the first jaw pitch-rotates.

3. The end tool of claim 1, wherein, when the first jaw rotates in response to rotation of the second jaw, the first jaw pitch-rotates at a same rotation angle as a rotation angle of the second jaw or pitch-rotates at a rotation angle of a preset ratio with respect to the rotation angle of the second jaw.

4. The end tool of claim 1, wherein the second jaw rotation shaft shares a same axis as the pitch rotation shaft.

5. The end tool of claim 4, wherein, when the first jaw rotates in response to rotation of the second jaw, the first jaw pitch-rotates at a same rotation angle as a rotation angle of the second jaw.

6. The end tool of claim 1, wherein a rotation angle range of the second jaw is +90° to −90° based on an extension direction (an X-axis) of the connection part, a rotation angle range of the first jaw is $+90-\theta_1$° to $-90-\theta_1$° based on the extension direction (the X-axis) of the connection part, and $\theta_1$ is an angle between the first jaw and the second jaw during opening operation.

7. The end tool of claim 1, wherein the end tool includes a first function that implements the opening or closing operation of the first jaw and the second jaw by the first jaw rotating about the pitch rotation shaft in response to the second jaw rotating about the second jaw rotation shaft, and a second function that implements the opening or closing operation of the first jaw and the second jaw by the second jaw rotating while the first jaw is fixed, wherein the end tool is selected and driven by one of the first function and the second function.

8. The end tool of claim 1, further comprising:

an end tool hub connecting the connection part to the first jaw and the second jaw, wherein the end tool hub includes:

a first end tool hub formed to accommodate at least a portion of the first jaw therein; and a second end tool hub axially coupled to the first end tool hub and rotatable relative to the first end tool hub.

9. The end tool of claim 8, wherein the first end tool hub and the second end tool hub are axially coupled through the pitch rotation shaft, and the end tool hub includes:

a pitch pulley rotatable about the pitch rotation shaft; and a pitch wire at least partially wound around the pitch pulley to transmit driving force to the pitch pulley.

10. The end tool of claim 9, wherein the pitch pulley includes a coupling part fixedly coupling the pitch pulley to the first end tool hub, and the first end tool hub rotates integrally with the pitch pulley by the coupling part.

11. The end tool of claim 9, further comprising:

a fastening member coupled to the pitch wire to couple the pitch pulley to the pitch wire.

12. The end tool of claim 11, wherein the pitch wire is formed as a single wire, and the fastening member is fastened to a portion of the pitch wire.

13. The end tool of claim 11, wherein the pitch pulley includes a fastening recess to which the fastening member is coupled.

14. The end tool of claim 13, wherein, when the end tool is in a neutral state, an imaginary line connecting a center of the pitch pulley to the fastening recess forms an angle of 0° to +90° with an extension direction (the X-axis) of the connection part.

15. The end tool of claim 9, wherein the end tool hub includes:

an auxiliary pulley rotation shaft parallel to the pitch rotation shaft and located adjacent to the pitch rotation shaft; and a pitch auxiliary pulley rotating about the auxiliary pulley rotation shaft.

16. The end tool of claim 15, wherein both strands of the pitch wire wound around the pitch pulley and extending to the connection part are disposed on a same side with respect to the auxiliary pulley rotation shaft.

17. The end tool of claim 15, wherein the pitch wire is located on a common internal tangent line of the pitch pulley and the pitch auxiliary pulley, a rotation angle of the pitch pulley is expanded by the pitch auxiliary pulley, and a rotation angle range of the second jaw is expanded by an additional angle set by the pitch auxiliary pulley.

18. The end tool of claim 8, wherein the first end tool hub and the first jaw are axially coupled through the pitch rotation shaft, and the end tool hub includes:

a pitch pulley rotatable about the pitch rotation shaft; and a pitch wire at least partially wound around the pitch pulley to transmit driving force to the pitch pulley.

19. A surgical instrument comprising:

an end tool rotatable in two or more directions;

a manipulation part controlling rotation of the end tool; and a connection part extending in a first direction (an X-axis) and having one end portion to which the end tool is coupled and another end portion to which the manipulation part is coupled, wherein the end tool includes:

a first jaw rotatable about a pitch rotation shaft; and a second jaw relatively rotatable with respect to the first jaw about a second jaw rotation shaft disposed in the first jaw and parallel to the pitch rotation shaft, wherein the first jaw and the second jaw are opposed to each other and perform an opening or closing operation, and the first jaw rotates about the pitch rotation shaft but rotates in a direction opposite to a rotation direction of the second jaw in response to the second jaw rotating about the second jaw rotation shaft.

* * * * *